(12) United States Patent
Doerr

(10) Patent No.: US 11,285,330 B2
(45) Date of Patent: Mar. 29, 2022

(54) HOUSING FOR AN IMPLANTABLE MEDICAL DEVICE

(71) Applicant: BIOTRONIK SE & Co. KG, Berlin (DE)

(72) Inventor: Thomas Doerr, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 12 days.

(21) Appl. No.: 16/774,429

(22) Filed: Jan. 28, 2020

(65) Prior Publication Data

US 2020/0282220 A1    Sep. 10, 2020

(30) Foreign Application Priority Data

Mar. 7, 2019 (DE) .................... 10 2019 105 798.1
Apr. 11, 2019 (EP) .................................. 19168592

(51) Int. Cl.
| | | |
|---|---|---|
| *A61N 1/37* | (2006.01) | |
| *A61N 1/375* | (2006.01) | |
| *A61N 1/39* | (2006.01) | |
| *A61B 17/34* | (2006.01) | |

(52) U.S. Cl.
CPC ......... *A61N 1/375* (2013.01); *A61N 1/37512* (2017.08); *A61N 1/3956* (2013.01); *A61N 1/3968* (2013.01); *A61B 17/3468* (2013.01)

(58) Field of Classification Search
CPC ..................................................... A61N 1/375
See application file for complete search history.

(56) References Cited

U.S. PATENT DOCUMENTS

| | | | |
|---|---|---|---|
| 9,123,470 B2 | 9/2015 | Sherwood et al. | |
| 2007/0060980 A1* | 3/2007 | Strother | A61N 1/0551 |
| | | | 607/61 |
| 2016/0263384 A1 | 9/2016 | Stevenson et al. | |

FOREIGN PATENT DOCUMENTS

WO        9302742 A2    2/1993

* cited by examiner

*Primary Examiner* — Eric D. Bertram
(74) *Attorney, Agent, or Firm* — Buchanan Ingersoll & Rooney PC

(57) ABSTRACT

A device housing for an IMD is suggested, the device housing having:
  a front side,
  a flat end face that is arranged perpendicular to the front side and connects to a straight upper edge of the front side,
  the front side having a maximum width (Bmax) that is measured parallel to the straight upper edge, and a maximum height (Hmax) that is measured perpendicular to the straight edge,
  wherein the ratio R of maximum width (Bmax) to maximum height (Hmax), i.e., Bmax/Hmax, is between 1.05 and 1.35.

10 Claims, 5 Drawing Sheets

HOUSING FOR AN IMPLANTABLE MEDICAL DEVICE

CROSS-REFERENCE TO RELATED APPLICATIONS

This patent application claims the benefit of and priority to co-pending German Patent Application No. DE 10 2019 105 798.1, filed Mar. 7, 2019 in the German Patent Office, and European Patent Application No. EP 19168592.4, filed Apr. 11, 2019 in the European Patent Office, which are hereby incorporated by reference in their entireties.

TECHNICAL FIELD

The present invention relates to a housing for an implantable medical device (IMD).

BACKGROUND

Housings for IMDs house the most important device components and protect them from the environment at the implantation site. The device housings may have external interfaces, e.g., for connecting device components electrically and mechanically (for example, for stimulation electrodes for cardiac pacemaker implants), or may have sensor interfaces for measuring body parameters.

There are IMDs whose device housings are implanted in a skin or tissue pocket of the patient (for example, for cardiac pacemaker implants or spinal cord stimulators). The device housings should be dimensioned as small as possible and should be shaped such that they do not cause discomfort to the patient. Known from the prior art are flat, rounded housing shapes that cause a slight bulge in the skin that projects outward as little as possible.

As a rule, cardiac pacemakers, implantable cardioverter-defibrillators (ICD), and CRT (cardiac resynchronization therapy) devices have a flat, rounded housing made of metal. The housing is mechanically connected to a header component (hereinafter referred to as a header) that typically comprises cast epoxy resin and provides the connectors for the electrode leads. Electrical lines lead out of the device housing into the header to the connectors for the electrode leads and in this way provide the electrical connection between electrodes and the components arranged in the interior of the housing, such as the device processor, battery, or, in the case of ICDs, the shock capacitor. The device housing with header is implanted in the upper chest region, above the ribs, below the clavicle, in a skin or tissue pocket. The device housing connected to the header is called the housing arrangement in the following.

Cardiac pacemakers, ICDs, and CRT devices are known in the prior art in which the housing arrangement, made of device housing and header, is embodied flat and has a circular outer contour. One problem with such housing arrangements is that they can easily rotate in the skin or tissue pocket. The electrode leads connected to the header turn at the same time, which can result in the electrode breaking.

Also known are housing arrangements in which the device housing is wider than it is high, or is higher than it is wide. One drawback of such housing arrangements is that the device housing tends to "wobble" on the ribs of the patient. The wobbling is caused by the space between the ribs of the patient and the device housing, this space being relatively large for such housing arrangements, since the device housing has a relatively long flat side that does not follow the contour of the ribs. The "wobbling" is pronounced and uncomfortable, in particular in patients having a small ribcage, the rib contours of which have a smaller circular radius.

During implantation of such housing arrangements, a comparatively small incision is made into the patient's skin, and this is associated with the drawback that the doctor has a limited amount of space for fashioning the skin or tissue pocket.

The present invention is directed at overcoming one or more of the above-mentioned problems.

SUMMARY

An underlying object of the present invention is to provide a device housing for an IMD that is comfortable for the patient to have under his skin, i.e., it is pain-free and essentially has no perceptible tensile or tugging forces. It is also an object of the present invention to provide a device housing for an IMD that "wobbles" as little as possible when it is implanted above the ribs of the patient.

One further object of the present invention is to provide a device housing for an IMD that does not easily rotate when implanted.

It is a further object of the present invention to provide a device housing for an IMD that may be implanted in a simple, rapid, and controlled manner.

At least these objects are attained using an inventive device housing according to claim 1, using a housing device comprising the device housing according to claim 12, and using a method for implanting the housing arrangement according to claim 14.

Advantageous exemplary embodiments of the present invention are found in the dependent claims.

According to the inventive solution, a device housing for an IMD is suggested, the device housing having:
- a front side,
- a flat end face that is arranged perpendicular to the front side and connects to a straight upper edge of the front side,
- the front side having a maximum width (Bmax) that is measured parallel to the straight upper edge, and a maximum height (Hmax) that is measured perpendicular to the straight edge,
- wherein the ratio R of maximum width (Bmax) to maximum height (Hmax), i.e., Bmax/Hmax, is between 1.05 and 1.35.

In this manner, the suggested device housing has optimal geometry to be comfortable for the patient when in use, i.e., the "wobbling" on the ribs is prevented or sharply reduced, since the device housing does not have a long surface. At the same time, rotation in the skin or tissue pocket is prevented because the housing is not circular.

According to one advantageous exemplary embodiment, the ratio R, i.e., Bmax/Hmax, is between 1.1 and 1.30, or is between 1.15 and 1.275, or is between 1.2 and 1.275; or is 1.25.

Moreover, according to advantageous aspects of the present invention, the front side has a maximum width (Bmax) of 40 mm to 70 mm, or of 50 mm to 65 mm, or of 55 mm to 65 mm, or of 60 mm.

According to further exemplary embodiments of the present invention, the front side has a maximum height (Hmax) of 40 mm to 70 mm, or of 40 mm to 60 mm, or of 45 mm to 55 mm, or of 45 mm to 52 mm, or of 48 mm.

The aforesaid dimensions for ratio R, Bmax, and Hmax have proven to be particularly effective for attaining at least the aforesaid objects.

Moreover, according to another aspect of the present invention, the device housing has a maximum thickness Dmax, the thickness being measured perpendicular to the plane of the front side, and the maximum thickness being from 9 mm to 15 mm, or from 9 mm to 12 mm, or from 10 mm to 11 mm, or being 10 mm.

The aforesaid thicknesses permit an ergonomic, thin device housing, with sufficient interior volume for housing the device components, if other geometries according to the suggestion are selected for the device housing in combination.

According to other advantageous embodiments of the inventive solution, the device housing has a back side that is arranged congruent with and opposing the front side, and wherein the flat end face connects to a straight upper edge of the back side. The device housing may also comprise two housing shells, the first housing shell having the front side and the second housing shell having the back side, the first and second housing shells being embodied symmetrically.

In this way it is possible for the device housing to have a symmetrical structure. A symmetrical structure is advantageous for patients that have an IMD implanted on the right side, instead of on the left side. Thus the IMD with the inventive device housing is simply turned around and may be implanted in a mirror-image, so that it has the same properties in terms of comfort for the patient as for a typical patient with the IMD implanted on the left side.

Moreover, according to advantageous aspects of the present invention, the outer contour of the front side of the device housing has curves with at least two different curve radii. A maximum curve radius of 12 cm, or 11 cm, or 10 cm, or 9.5 cm is not exceeded.

The selection of the curve radii ensures that the implant does not have any long surfaces, so that "wobbling" on the ribs is prevented.

According to advantageous embodiments of the present invention, the ratio of the surface area of the front side to the surface area of a rectangle that spans the maximum width (Bmax) and maximum height (Hmax) of the front side, i.e., $$\frac{\text{surface area (front side)}}{\text{surface area (back side)}},$$

is at least 0.6, or at least 0.7, or at least 0.75, or at least 0.8, or at least 0.85, or at least 0.9, or at least 0.95.

Moreover, the ratio of the surface area of the front side to the surface area of an ellipse that spans maximum width (Bmax) and maximum height (Hmax) of the front side, i.e., $$\frac{\text{surface area (front side)}}{\text{surface area (ellipse)}},$$

is at most 1.5, or at most 1.4, or at most 1.3, or at most 1.2, or at most 1.15, or at most 1.1.

Selecting the "fill factor" according to the suggestion ensures that, for one thing, the shape of the device housing is "somewhat circular" or at least "somewhat elliptical" so that sharp corners in the contour and long surfaces are prevented in order to increase comfort and to prevent "wobbling."

According to other aspects of the present invention, the device housing has rounded edges. These increase wearing comfort for the patient.

According to other embodiments, in addition a housing arrangement for an IMD is suggested that comprises an inventive device housing and a header (3). The header is connected to the device housing at the flat end face of the device housing.

According to advantageous embodiments of the present invention, the IMD is a cardiac pacemaker, an implantable cardioverter defibrillator, or a CRT device.

In addition, a method for implanting an inventive housing arrangement is suggested. The method comprises the steps:
Providing the housing arrangement,
Opening the body tissue of a patient below the clavicle by means of an incision,
Preparing a tissue pocket that approximately corresponds in size to the volume of the housing arrangement,
Inserting the device housing into the tissue pocket, and
Closing the tissue pocket.

According to one advantageous aspect of the inventive method, the length of the incision is less than or equal to the maximum width (Bmax) of the front side of the device housing. Alternatively, the length of the incision may be less than or equal to the maximum height (Hmax) of the front side plus the height of the header. In this way the incision made has the optimum length for preparing a skin or tissue pocket.

Additional features, aspects, objects, advantages, and possible applications of the present invention will become apparent from a study of the exemplary embodiments and examples described below, in combination with the Figures, and the appended claims.

DESCRIPTION OF THE DRAWINGS

Additional advantageous embodiments may be found in the figures and descriptions of the figures. The figures illustrate different aspects of the invention and should not be considered as limiting for the protected subject matter.

DETAILED DESCRIPTION

Figure 1:
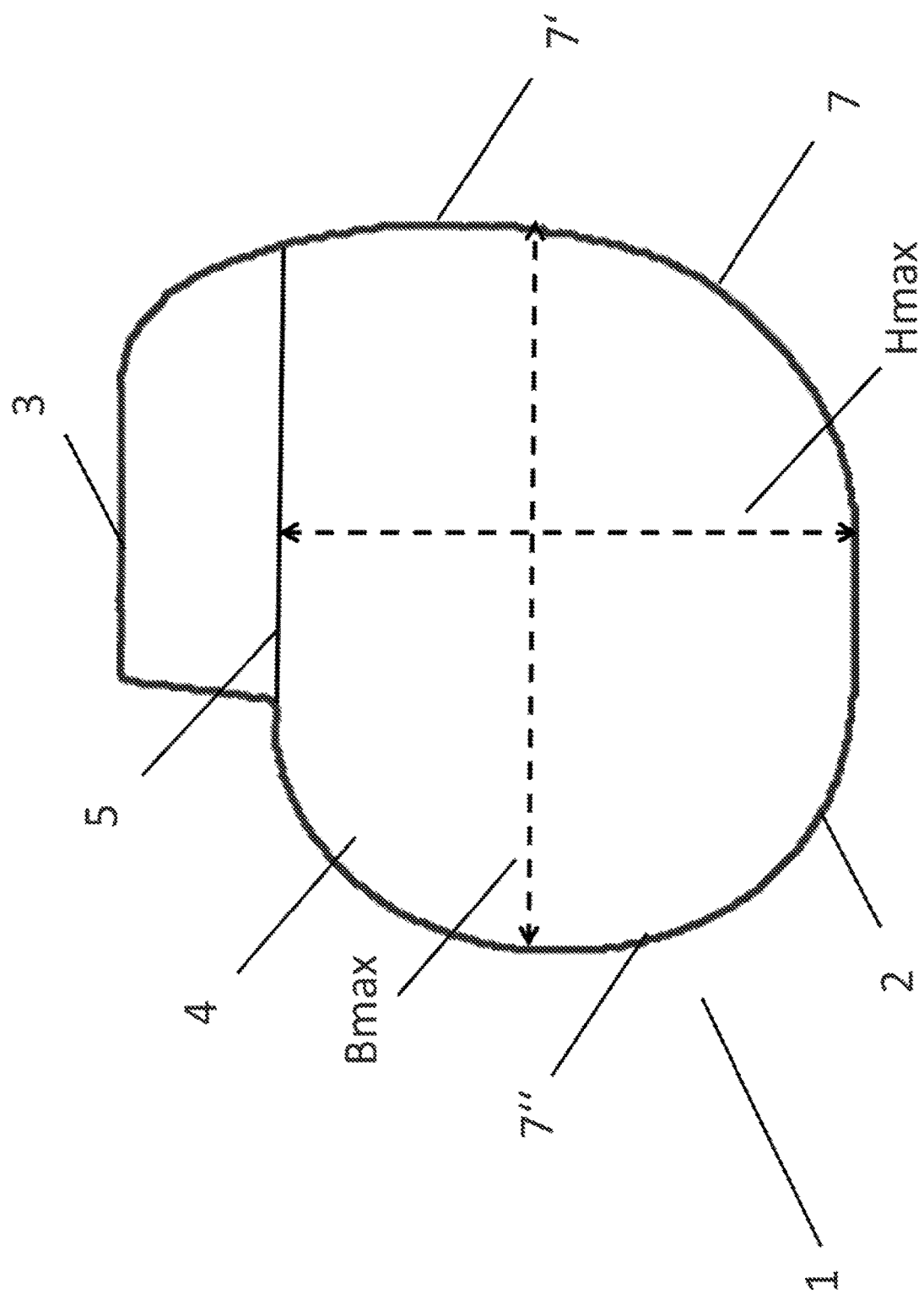
FIG. 1 is a schematic view of a housing arrangement according to the present invention.

FIG. 1 illustrates the contours of an inventive housing arrangement 1, comprising device housing 2 and header 3. The device housing 2 has a front side 4 and a flat end face 6 that is arranged perpendicular to the front side 4 and connects to a straight upper edge 5 of the front side. The front side 4 has a maximum width Bmax that is measured parallel to the straight upper edge 5. The front side 4 also has a maximum height Hmax that is measured perpendicular to the straight upper edge 5. The outer contour of the front side 4 comprises curves having at least two different curve radii 7, 7', 7".

Figure 2:
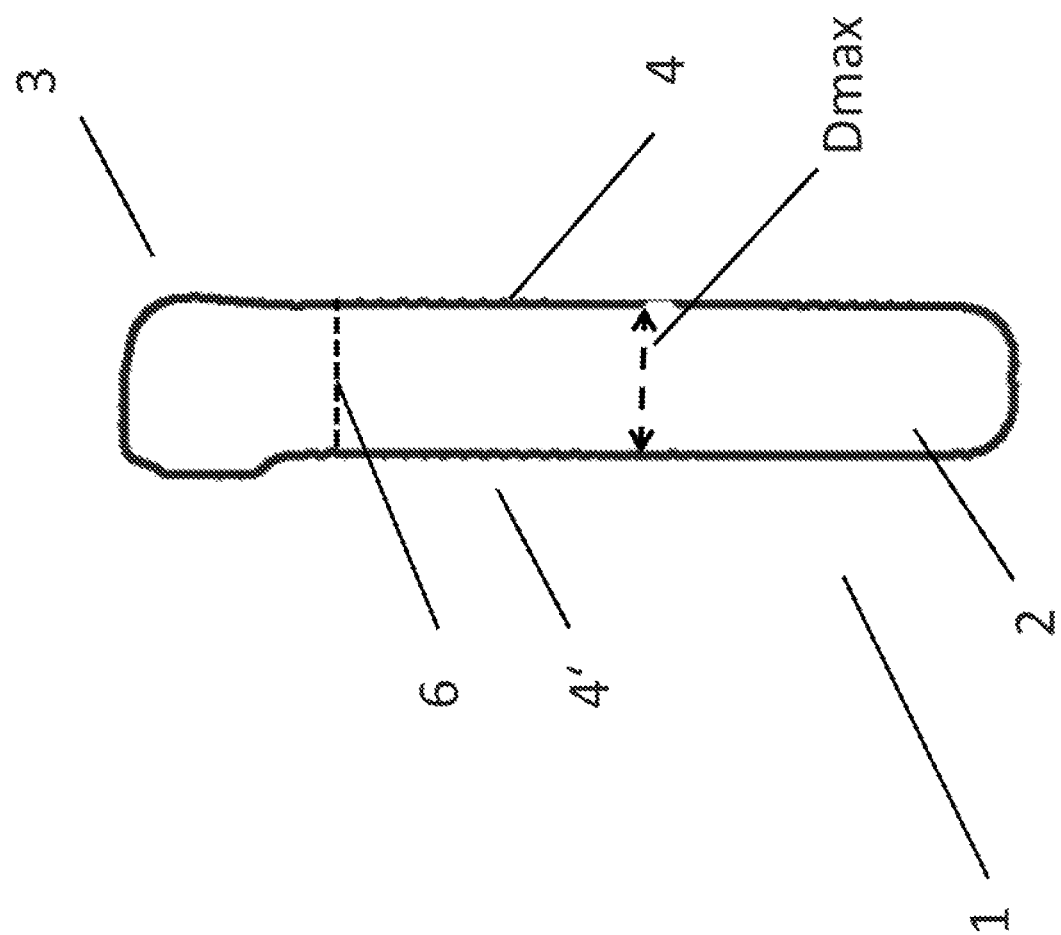
FIG. 2 is a schematic side view of a housing arrangement according to the present invention.

FIG. 2 is a schematic side view of the inventive housing arrangement. The maximum thickness Dmax of the device housing, which is measured perpendicular to the front side 4, may be seen. The device housing 2 also has a back side 4' that may be configured congruent with the front side 4.

Figure 3:
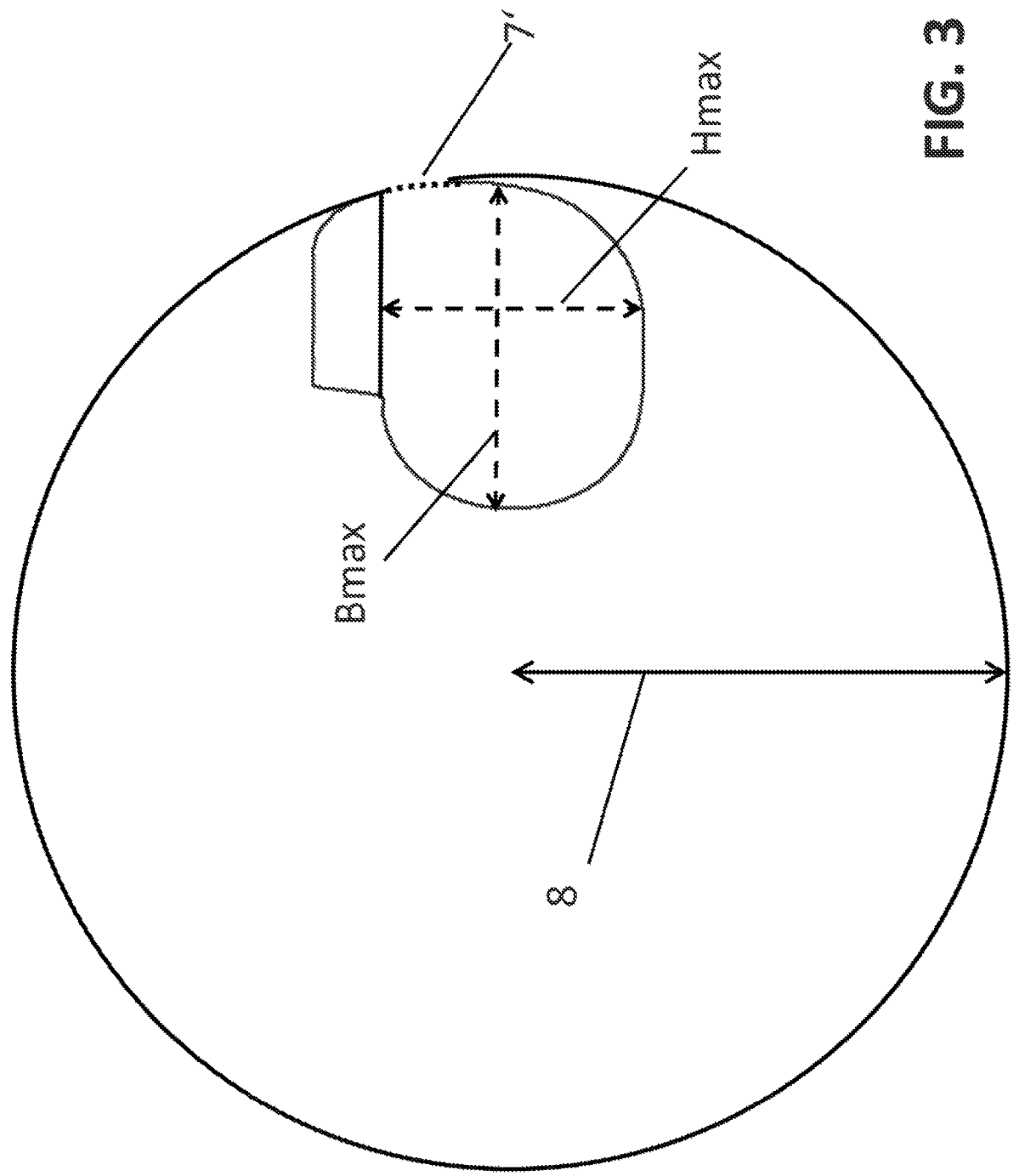
FIG. 3 is a schematic representation of how the curve radius for the contour of the device housing is determined.

FIG. 3 schematically illustrates a measurement of the curve radius 7'. The corresponding circle segment is shown with a broken line. A circle with a corresponding circle segment is overlaid and the circle radius 81 corresponds to the curve radius 7'.

Figure 4:
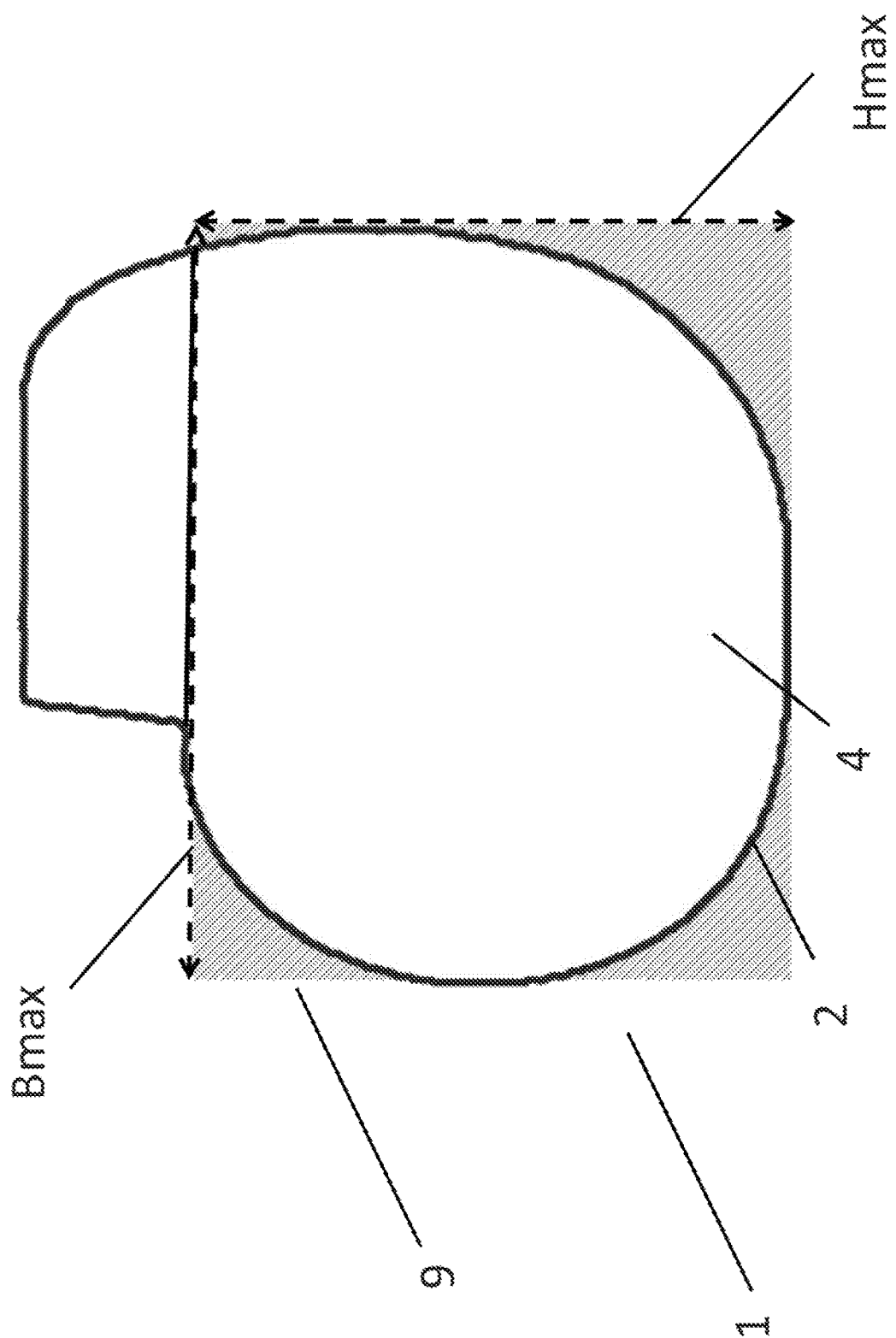
FIG. 4 is a schematic representation of how a fill factor for the surface area of the front side of the device housing is determined.

FIG. 4 schematically illustrates how the fill factor, which is found using the ratio of the surface area of the front side 4 to a rectangle 9 that spans Bmax and Hmax, is determined. The shaded area corresponds to the portion of the rectangular surface area that is not filled by the surface area of the front side 4.

Figure 5:
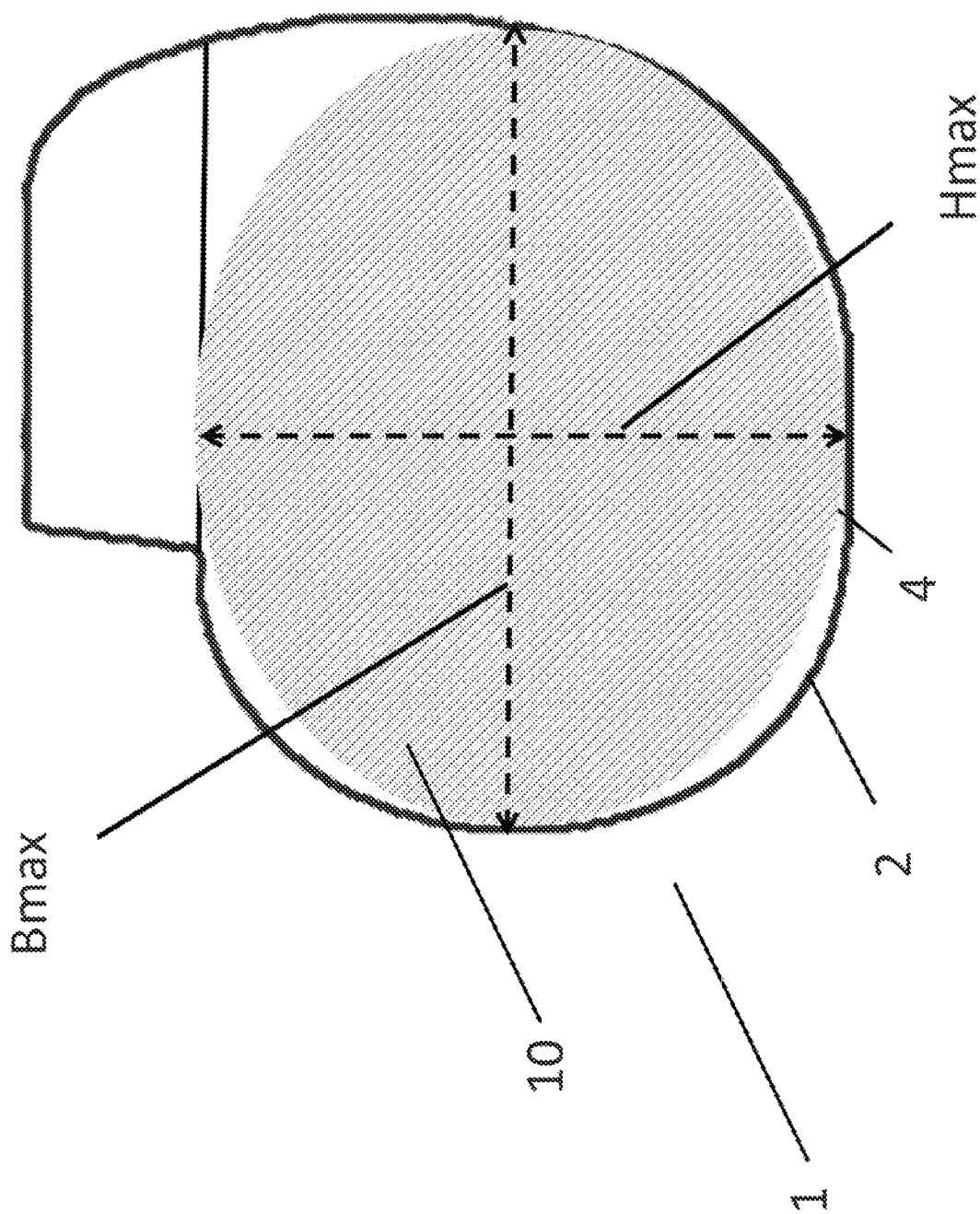
FIG. 5 is a schematic representation of how a fill factor for the surface area of the front side of the device housing is determined.

FIG. 5 schematically depicts how the fill factor that is found using the ratio of the surface area of the front side 4 to an ellipse 10 that has Bmax and Hmax as principle axis and secondary axis is determined. The area of the front side 4 not covered by the shaded surface area corresponds to the portion of the surface area that projects beyond the ellipse.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

I claim:

1. A housing arrangement for an implantable medical device (IMD) comprising:
    a device housing comprising:
        a front side,
        a flat end face that is arranged perpendicular to the front side and connects to a straight upper edge of the front side,
        the front side having a maximum width (Bmax) that is measured parallel to the straight upper edge, and a maximum height (Hmax) that is measured perpendicular to the straight upper edge,
        wherein the ratio R of maximum width (Bmax) to maximum height (Hmax), Bmax/Hmax, is between 1.15 and 1.275,
        wherein the ratio of the surface area of the front side to the surface area of a rectangle that spans the maximum width (Bmax) and maximum height (Hmax), $$\frac{\text{surface area (front side)}}{\text{surface area (rectangle)}},$$

is at least 0.6,
    and wherein the IMD is a cardiac pacemaker, an implantable cardioverter, or a cardiac resynchronization therapy (CRT) device; and
    a header, wherein the header is connected to the device housing at the flat end face.

2. The housing arrangement according to claim 1, wherein R is selected from the group consisting of: between 1.1 and 1.30, between 1.15 and 1.275, between 1.2 and 1.275, and is 1.25.

3. The housing arrangement according to claim 1, wherein the maximum width (Bmax) is selected from the group consisting of: from 40 mm to 70 mm, from 50 mm to 65 mm, from 55 mm to 65 mm, and is 60 mm.

4. The housing arrangement according to claim 1, wherein the maximum height (Hmax) is selected from the group consisting of: from 40 mm to 70 mm, from 40 mm to 60 mm, from 45 mm to 55 mm, from 45 mm to 52 mm, and is 48 mm.

5. The housing arrangement according to claim 1, wherein the device housing has a maximum thickness (Dmax), the thickness being measured perpendicular to the plane of the front side, and the maximum thickness selected from the group consisting of: from 9 mm to 15 mm, from 9 mm to 12 mm, from 10 mm to 11 mm, and being 10 mm.

6. The housing arrangement according to claim 1, wherein the device housing has a back side that is arranged congruent with and opposing the front side, and wherein the flat end face connects to a straight upper edge of the back side.

7. The housing arrangement according to claim 6, wherein the d.evke housing comprises two housing shells, the first housing shell having the front side and the second housing shell having the back side, the first and second housing shells being embodied symmetrically.

8. The housing arrangement according to claim 1, wherein the outer contour of the front side has curves with at least two different curve radii, wherein a maximum curve radius selected from the group consisting of: 12 cm, 11 cm, 10 cm, and 9.5 cm, is not exceeded.

9. The housing arrangement according to claim 1, wherein the ratio of the surface area of the front side to the surface area of an ellipse that spans maximum width (Bmax) and maximum height (Hmax)

$$\frac{\text{surface area (front side)}}{\text{surface area (ellipse)}},$$

is selected from the group consisting of: at most 1.5, at most 1.4, at most 1.3, at most 1.2, at most 1.15, and at most 1.1.

10. The housing arrangement according tc claim 1, wherein the device housing has rounded edges.

* * * * *